United States Patent [19]

Kelley et al.

[11] Patent Number: 5,695,524
[45] Date of Patent: Dec. 9, 1997

[54] CONSTANT WIDTH, ADJUSTABLE GRIP, STAPLE APPARATUS AND METHOD

[75] Inventors: Mark Kelley; Phil McDuffie, both of Austin, Tex.

[73] Assignee: Tracor Aerospace, Inc., Austin, Tex.

[21] Appl. No.: 538,001

[22] Filed: Oct. 2, 1995

Related U.S. Application Data

[63] Continuation of Ser. No. 222,887, Apr. 5, 1994, abandoned.

[51] Int. Cl.$^6$ .................................................. A61B 17/04
[52] U.S. Cl. .................. 606/219; 227/902; 411/471; 411/920; 411/457
[58] Field of Search ................... 29/432.1, 812; 411/471, 457, 473, 920, 921; 227/902; 606/219

[56] References Cited

U.S. PATENT DOCUMENTS

| | | | |
|---|---|---|---|
| 275,435 | 4/1883 | Sweet, Jr. | 411/920 X |
| 1,039,531 | 9/1912 | Hartley | 411/457 X |
| 1,193,502 | 8/1916 | Bingham | 411/457 X |
| 1,264,238 | 4/1918 | Whetstone | 411/457 X |
| 2,008,086 | 7/1935 | Sorenson | 29/432.1 |
| 2,778,266 | 1/1957 | Forrester | 411/920 X |
| 4,505,273 | 3/1985 | Braun . | |
| 4,607,638 | 8/1986 | Crainich | 606/219 |
| 4,802,478 | 2/1989 | Powell . | |
| 4,874,122 | 10/1989 | Froelich et al. . | |
| 4,887,601 | 12/1989 | Richards . | |
| 4,899,745 | 2/1990 | Laboureau et al. | 411/457 X |
| 5,158,567 | 10/1992 | Green . | |
| 5,222,975 | 6/1993 | Crainich . | |
| 5,236,440 | 8/1993 | Hlavacek . | |

FOREIGN PATENT DOCUMENTS

| | | | |
|---|---|---|---|
| 503271 | 9/1992 | European Pat. Off. | 606/219 |

Primary Examiner—Joseph M. Gorski
Attorney, Agent, or Firm—Shaffer & Culbertson; J. Nevin Shaffer, Jr.

[57] ABSTRACT

A staple and stapler for injecting the staple in a manner so that the staple maintains a near constant width upon penetration of material to be joined and during staple closure/forming such that material perturbation and staple to staple spacing may be minimized. The staple has a rectilinear bridge part from which depend oppositely positioned side parts and from the side parts a pair of straight legs. In a preferred embodiment, the oppositely positioned side parts consist of a proximal arcuate section attached to the bridge part and an oppositely directed distal arcuate section attached to the legs. The legs may have sharpened points. Also disclosed is a stapler adapted to force the oppositely directed distal arcuate sections outward, in one embodiment, thereby forcing a reaction of the legs of the staple to face each other in linear alignment and form a closed staple. The unpreloaded fully-formed staple may be deformed in situ by means of a preload part on a cam slide so as to create a U-shaped central portion for the compression of captured material. Alternatively, a preformed staple with the U-shaped central portion may also be used.

8 Claims, 8 Drawing Sheets

Figure 6
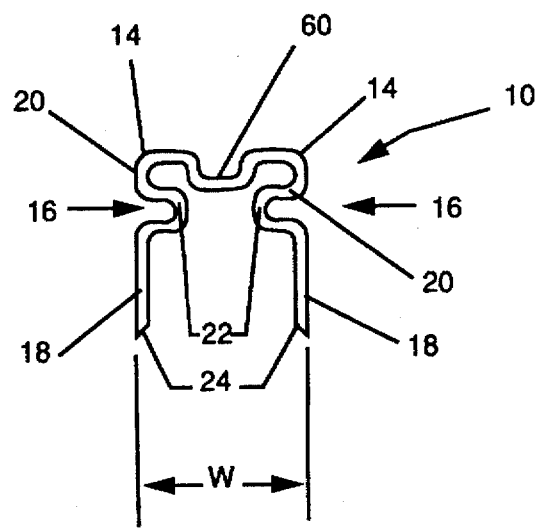
Figure 7
PRIOR ART
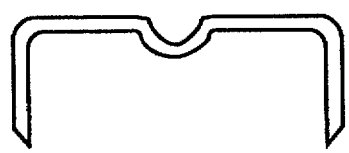
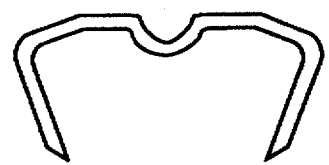
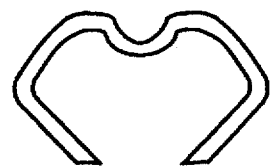
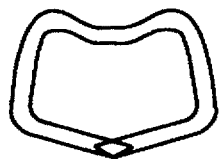

CONSTANT WIDTH, ADJUSTABLE GRIP, STAPLE APPARATUS AND METHOD

This application is a continuation of U.S. application Ser. No. 08/222,887, filed on Apr. 5, 1994, and now abandoned.

BACKGROUND OF THE INVENTION

This invention relates to an improved fastener that maintains a constant width while being formed from the open to the closed position. Further, this invention relates to a staple and stapling device wherein the length of the staple may be adjusted and the staple can be injected and formed without need for a far side anvil.

Staples and staplers and surgical staples and apparatus for inserting and removing them have been known in the art for quite some time. The typical surgical staple operates much the same as the common desk staple in that the extended legs of the staple are forced into an are as they are closed together to draw the tissue together. Examples of such staples are found in Hlavacek, U.S. Pat. No. 5,236,440; Crainich, U.S. Pat. No. 5,222,975; Green, U.S. Pat. No. 5,158,567; Richards, U.S. Pat. No. 4,887,601; Froelich et al., U.S. Pat. No. 4,874,122; Powell, U.S. Pat. No. 4,802,478; and Braun et al., U.S. Pat. No. 4,505,273. Each of these staples decrease in width as the staple is forced one way or another to the closed position. Many of these require some sort of anvil and, as in the ordinary stapler, some require a "far side" anvil so that the tissue is actually encompassed by the stapler.

A drawback to the staples and staplers known in the art is that when the staple decreases in width as the closed staple is formed, the material often tears along the curve of the staple, or at the point where the staple enters the material so as to accommodate the reduction in width of the staple as it is closed. A further drawback is related to the typical functioning of the prior art staple in that, because the staple involves a wider area of material from start to finish, close spacing of prior art staples is difficult or impossible to accomplish. Additionally, many designs require a separate anvil or dye to perform the staple forming closure and, as such, require access from the far side of the vessel attachment zone to realize attachment. This is another reason that often precludes prior art staples and/or staplers from use in some surgical procedures. This is of particular importance when performing end-to-side anastomosis of two vessels, for example, since the presence of an anvil inside the receiving artery cannot be tolerated because it would partially or completely occlude blood flow.

Thus, there is a need in the art for providing a staple and stapler such that the staple maintains a near constant width upon penetration of the material and during staple closure/forming such that material perturbation and staple to staple spacing may be minimized. Therefore, it is an object of this invention to provide an improved staple and stapler that maintains a near constant width upon penetration and during staple closure/forming.

SHORT STATEMENT OF THE INVENTION

Accordingly, the staple of the present invention includes a staple having a bridge part, with two ends, having two oppositely positioned side parts connected to two, spaced-apart a certain width, generally straight, legs. The oppositely positioned side-parts have a proximal arcuate section and a distal arcuate section and each of the proximal arcuate sections are joined to one of the ends of the bridge part. Each of the distal arcuate sections are joined to one of the legs. In one embodiment, the staple is closed by straightening the distal arcuate sections so that the legs are forced into linear facing alignment, while at the same time generally maintaining the original spaced-apart width. Another embodiment of the invention includes a staple where the bridge part has a generally U-shaped central portion having opposite ends and at least one arcuate part.

A stapler and stapler method is also provided which includes the staple as abovedescribed; an injector having a housing adapted to contain the staple and inject the staple into material to be joined; a spreader in the housing having two separate parts, each having an end part adapted to engage the open staple at the lower portion of the side part; reaction plates connected to the housing against which the staple is forced by the end parts of the spreader; and a cam device for moving the spreader to close the open staple. In another embodiment, the stapler includes a pre-loading part within the housing used to deform the rectilinear bridge part into a U-shape, after the staple is closed.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 6 shows a staple in the open position that is preformed to produce a preloaded state upon installation, i.e. no preloading step is required.

FIG. 7, labeled "Prior Art", shows the standard endoscopic staple of the prior art;

DESCRIPTION OF THE PREFERRED EMBODIMENTS

Figure 1:
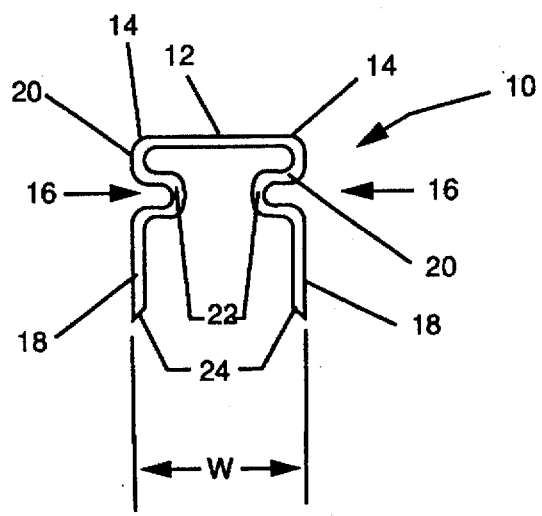
FIG. 1 is an elevational view of a preferred embodiment of a staple according to the present invention in the open position.

The preferred embodiment of the present invention is illustrated by way of example in FIGS. 1–6 and 8–13. With specific reference to FIG. 1, a staple 10 includes a bridge part 12, with two ends 14, having two oppositely positioned side parts 16, spaced-apart a certain width W, and straight legs 18. The oppositely positioned side-parts 16 have a proximal arcuate section 20 and an oppositely directed distal arcuate section 22. Each of the proximal arcuate sections 20 is joined to a corresponding bridge part end 14 and each of the oppositely directed distal arcuate sections 22 is joined to one of the corresponding legs 18. It will be understood that while staple 10 has been described in various parts it is anticipated that it will be formed from a single piece of rigid material and formed as described. Legs 18 may also include sharpened points 24.

Figure 2:
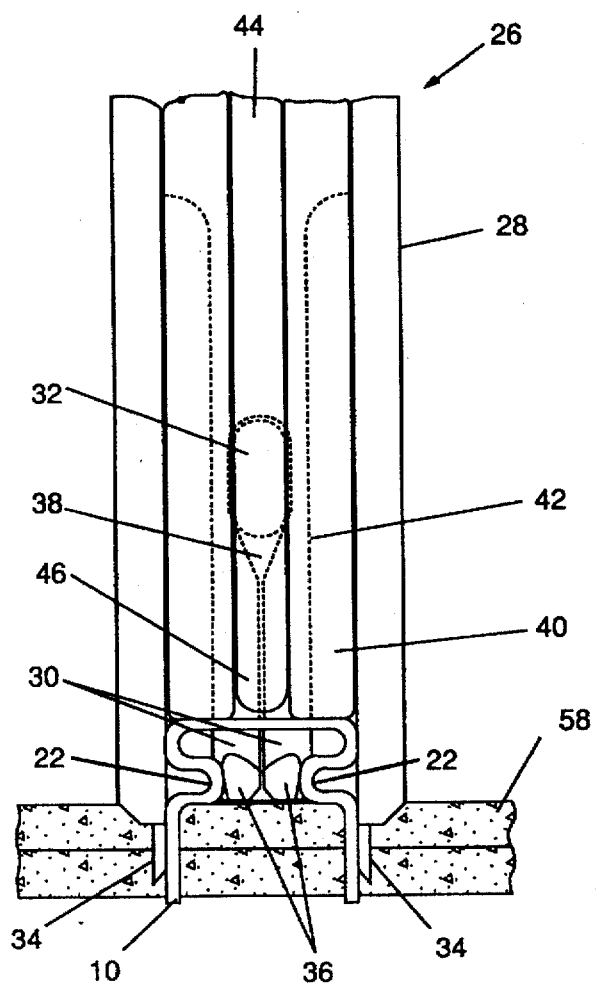
FIG. 2 shows the stapler and staple in the initial open state.
Figure 8:
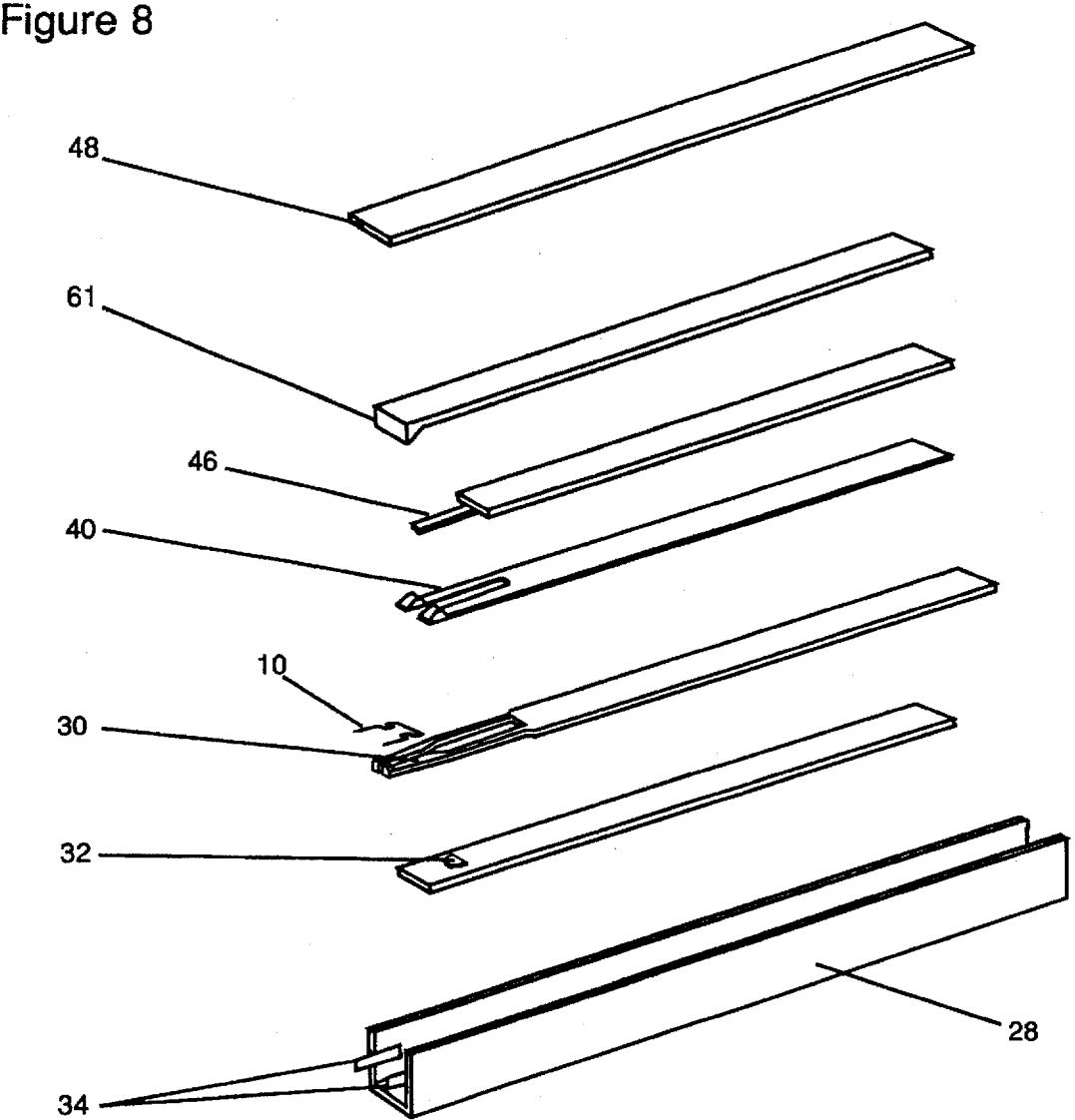
FIG. 8 is an exploded view of the stapler of the present invention.

Referring now to FIG. 2, the staple 10 of the present invention is shown located in stapler 26. Stapler 26 includes injector housing 28; cantilever spreader beams 30; cam 32 and reaction form 34. Cantilever spreader beams 30, each have an end part 36 adapted to engage the open staple 10 at the oppositely directed distal arcuate sections 22. FIG. 2 also discloses cam slide 38; injector slide 40; spreader slide 42; and preload slide 44. Further, preload die 46 located in from of cam 32 is also shown. FIG. 8, an exploded view reveals the previously disclosed parts as well as a cover plate 48.

Figure 3:
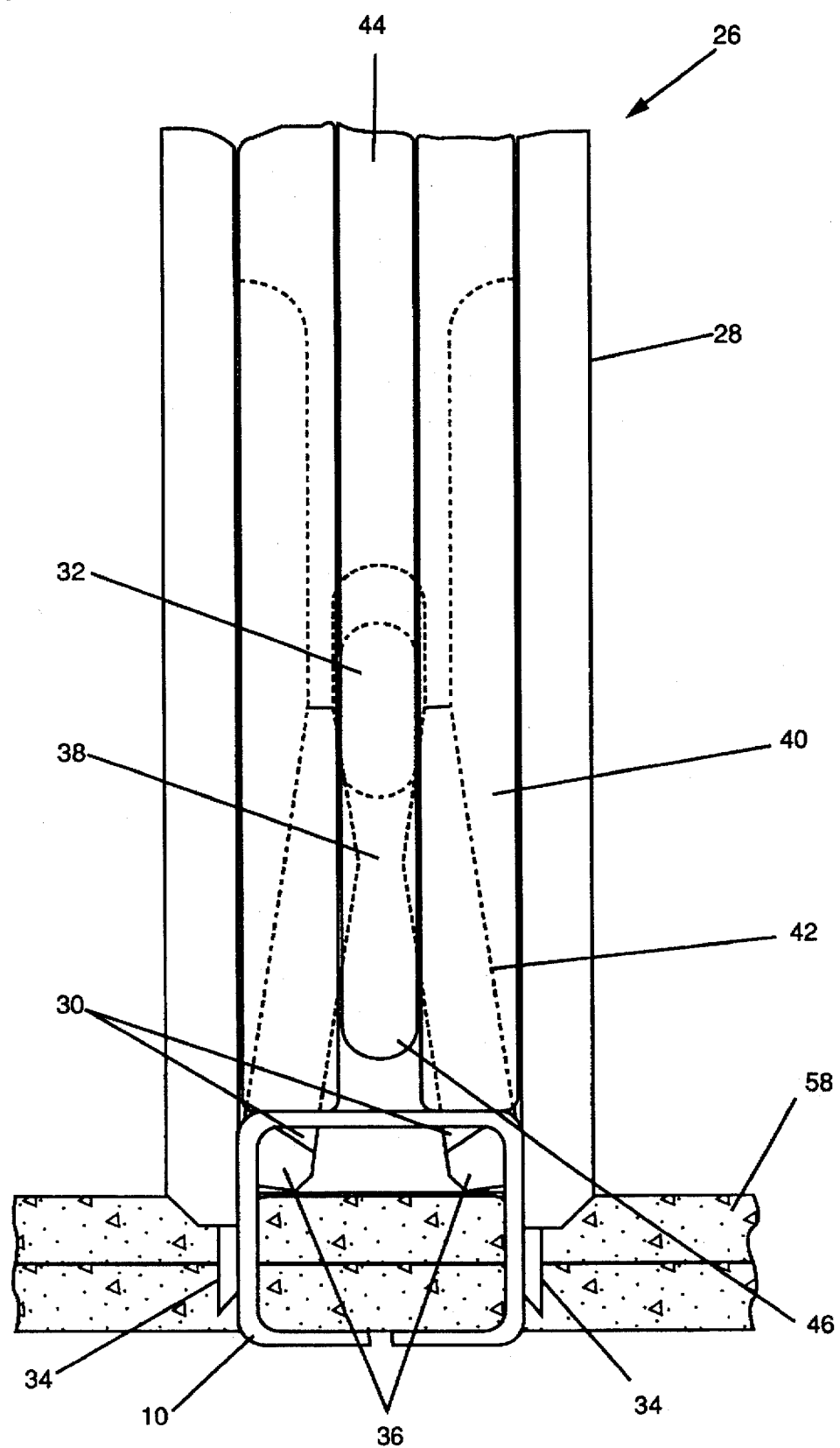
FIG. 3 shows the stapler and the staple in a formed state.

Referring now to FIG. 3, it shows that cam 32 has forced cantilever spreader beams 30 apart thereby forcing cantilever spreader end parts 36 against oppositely directed distal arcuate sections 22 of staple 10 which in response to reaction form 34, causes legs 18 to align themselves linearly. As a result, staple 10 reaches a formed or closed state and the original width "W" of the staple 10 has been maintained throughout the closing procedure.

Figure 4:
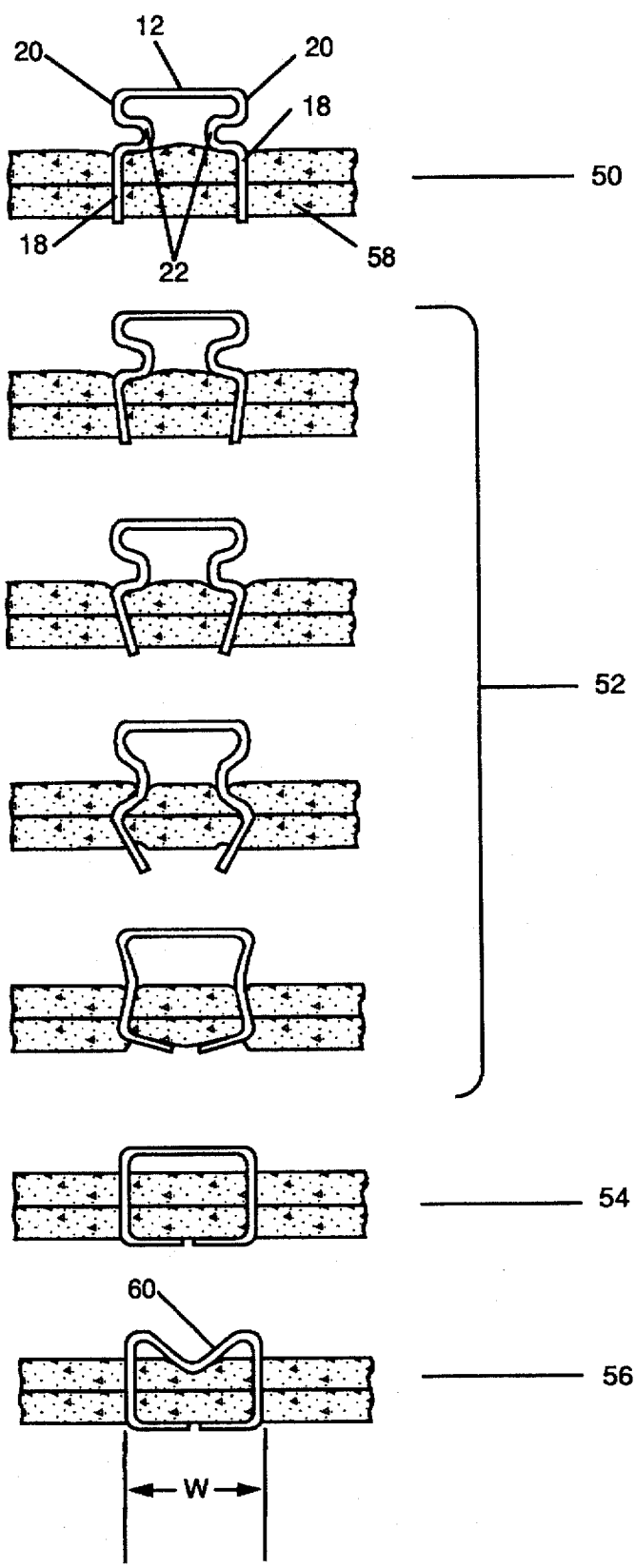
FIG. 4 is a top to bottom illustration of the staple forming sequence of the present invention.

The operation of the stapler 26 of the present invention may actually be more easily envisioned by reference to FIG. 4 which illustrates the staple forming sequence. The four stages of the staple forming sequence are initial staple condition 50, staple injection/forming sequence 52, unpreloaded fully-formed staple position 54, and preloaded condition 56. Initial staple condition 50 shows the staple 10 in its open condition with the rectilinear bridge part 12 and with the side parts 16 spaced apart an original width "W". The side parts 16 generally have a S-shape, with the upper curved portion of the S, the proximal arcuate section 20, facing inward and curving outward, connecting to one of the bridge part ends 14 and with the lower portion of the S, the oppositely directed distal arcuate section 22, facing outward and curving inward connected to a sight leg 18 so that the open staple 10 is symmetrical about the center of the rectilinear bridge part 12.

From top to bottom, the next four figures in FIG. 4 illustrate the staple injection/forming sequence 52. As can be seen, in the initial staple condition 50, the insertion of the staple 10 into the tissue 58, to be joined is accomplished, and is followed by the legs 18 passing completely through the tissue 58 although complete tissue penetration is not a requirement in every case. The action of the cantilever spreader end parts 36 in conjunction with the reaction form 34 can be envisioned as legs 18 are forced into linear alignment with sharp points 24 facing each other.

Figure 5:
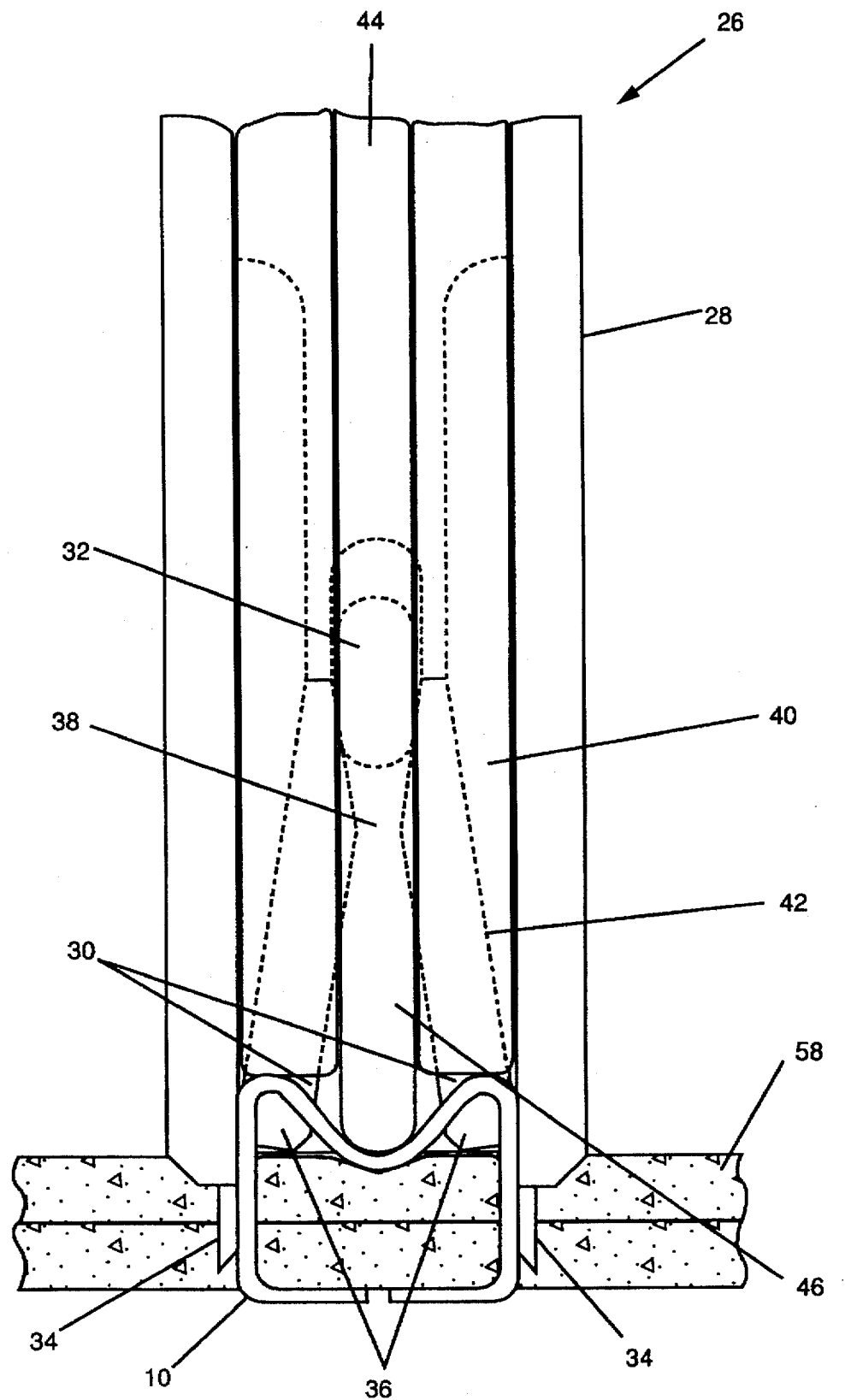
FIG. 5 is an illustration of the stapler preloading a staple.

Unpreloaded fully-formed staple position 54 presents a closed staple, the width "W" of which has not changed from the original width of the initial staple condition 50. Also illustrated is preloaded condition 56. Preloaded condition 56 is attained by utilization of preload die 46 of cam 32 to form a generally U-shaped central portion 60 of bridge part 12. The creation of preloaded condition 56 by means of stapler 26 is illustrated in FIG. 5. An alternate approach for staple preloading is to laterally load the tissue to induce a thinning effect due to lateral strain. Upon completion of the stapling sequence, the tissue stress state would be relieved, resulting in thickening in the tissue dimension being stapled and loading the staple.

By way of comparison, with reference to FIG. 7, the staple forming sequence of the Prior Art is illustrated wherein the width of the prior art staple dramatically decreases as the widely spaced legs go from the open to the closed position.

As can be determined from this disclosure, a preferred embodiment of the invention is a surgical staple and stapler designed for the purpose of performing small scale tissue attachments during surgical procedures. Each staple 10 is between 1.65mm and 2.0 mm in width and is constructed, preferably, of 150 micron diameter MP35N wire. The staple 10 is formed, preferably, of a single continuous segment of wire to produce the shape shown in FIG. 1. As a result the length of legs 18, and other dimensions, can be varied as desired.

FIG. 6 shows an alternative configuration of staple 10 that may be employed to facilitate post injection staple preloading, discussed further hereafter.

Figure 9:
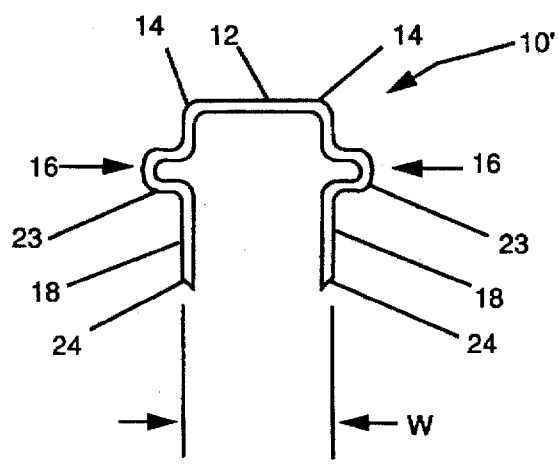
FIG. 9 is an elevational view of another preferred embodiment of a staple.
Figure 10:
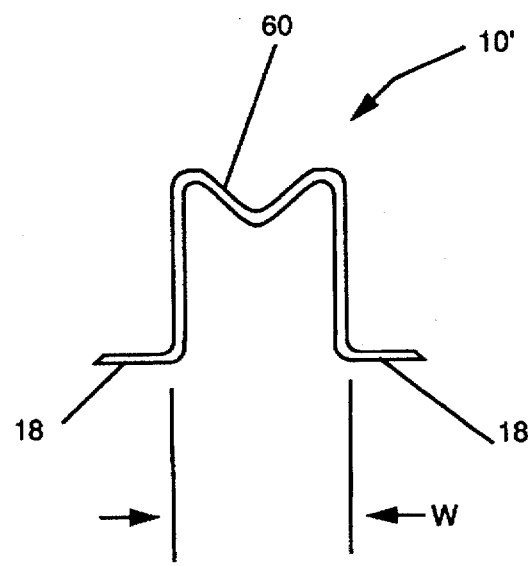
FIG. 10 shows the staple of FIG. 9 in a formed state.

Referring now to FIG. 9, another embodiment of the staple, 10', of the present invention is disclosed. As shown in FIG. 9, this staple 10' comprises a bridge part 12 with two ends 14 having two oppositely positioned side parts 16 connected to two spaced-apart a certain width legs 18. The oppositely positioned side parts 16 have an outward facing arcuate section 23 each connected to one of the legs 18. The staple 10' is closeable, in this embodiment, by straightening the outward facing arcuate sections 23 so that the legs 18 are forced into opposite facing linear alignment, while at the same time generally maintaining the original spaced-apart width. Referring to FIG. 10, staple 10' is shown in its fully formed position with legs 18 linearly aligned and oppositely facing. FIG. 10 also show staple 10' with a generally U shaped central portion 60 formed in bridge part 12.

Figure 11:
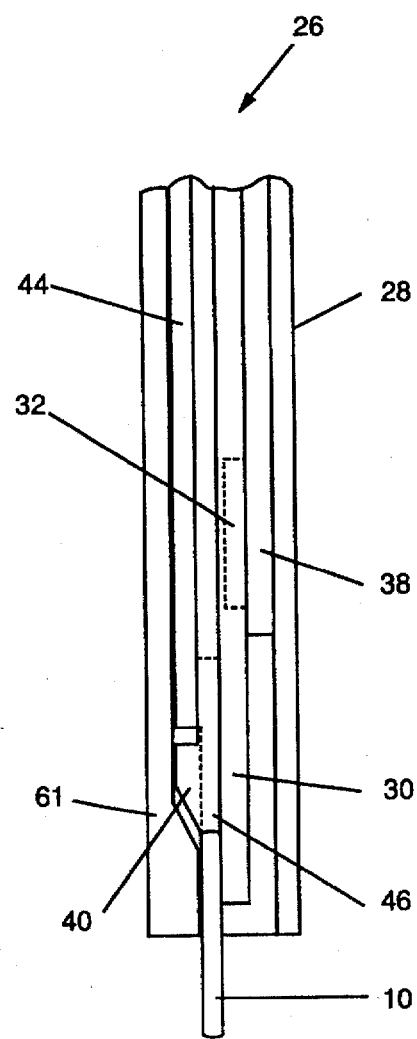
FIG. 11 is a side elevational view of the staple and stapler in the engaged position.
Figure 12:
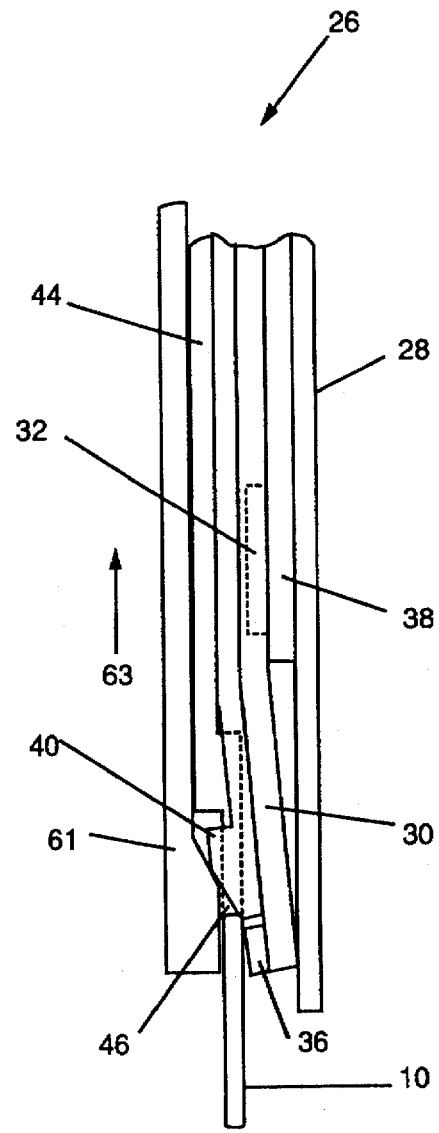
FIG. 12 is a side elevational view of the staple disengaged from the stapler.

Referring now to FIGS. 11 and 12, the operation of stapler 26 in disengaging staple 10 and/or staple 10', is illustrated. FIG. 11 shows top-slider 61 contained within the housing (not shown) in a position wherein the staple 10 has been fully formed and is still engaged by cantilever spreader beam 30. Referring to FIG. 12, it is illustrated that top slider 61 is moved in the direction of arrow 63, thereby forcing injector slide 40 and cantilever spreader beams 30 to depress and releasing the cantilever end parts 36 from engagement with staple 10. In this position, stapler 26 is now free to be removed from its location adjacent to the staple without fear that the staple 10 will be pulled back with stapler 26. Cam slide, 38, is retracted in direction 63 prior to retracting 61. This produces an open volume below spreader beam 30 to deflect into.

Figure 13:
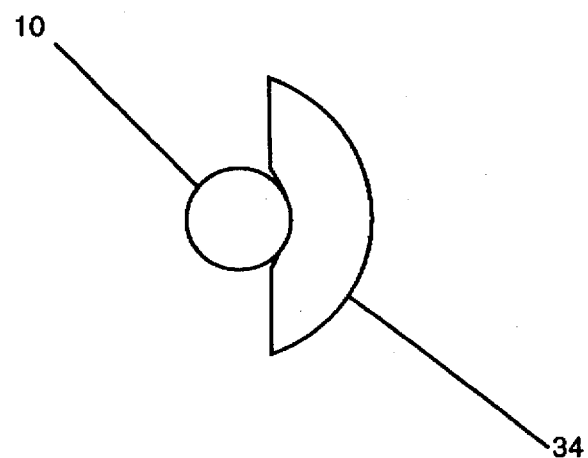
FIG. 13 is a top cross sectional view of one embodiment of a reaction plate.

Referring now to FIG. 13, another embodiment of the reaction form 34 of the present invention is illustrated. In this embodiment reaction plate 34 is formed in a shape that conforms to the circumference of staple 10 and/or 10'. As a result, staple 10 is partially encompassed by reaction plate 34. As a further result, reaction plate 34 also stabilizes staple 10 as stapler 26 is inserted and removed and stabilizes staple 10 against lateral motion. Further, in this embodiment, reaction plate 34 always insures proper staple formation and keeps the staple 10 in the proper plane for such formation. It should be noted that reaction form 34 may be formed from an azimuth section of a thin walled, right circular cylinder or tube whose end may be beveled to aid in tissue penetration, such as a hypodermic needle. In this case, reaction form 34 also acts as an aid in penetration of the tissue 58.

The stapler 26 performs four tasks in its role of exercising the staple 10 and/or 10'. These four tasks are staple capture, initial staple forming, staple pre-loading and staple release. Referring specifically to FIGS. 2, 3 and 5, the stapler 26 must first hold the staple 10 securely to allow placement on the tissue 58 without concern for dropping the staple 10. This state is illustrated in FIG. 2 where the staple 10 is captured between staple spreader end parts 36 and injection slide 40 to preclude vertical motion, the injector housing 28 to constrain lateral motion, and the spreader slide 42 and the top cover plate 48 (not shown) to keep the staple 10 in the desired plane.

In operation, the stapler 26, by means of injector slide 40, applies force to the staple 10 to induce injection into the tissue 58, or other material to be joined, at the desired location. The cam 32 and spreaders 30 work together to form the staple 10 into a closed rectangular form 54 that captures the tissue 58 between bridge part 12 and the now co-planer legs 18. The staple 10 may be injected such that the tissue 58 is completely penetrated or such that the distal side of the rectangular staple form falls within the tissue. In any event, the staple 10 and/or 10' maintains a near constant width "W" during the injection/forming process 52, by applying forces to the staple 10 to induce a plastic deformation that results in the unpreloaded fully-formed staple condition 54.

In particular, unpreloaded fully-formed staple condition 54 is produced by inducing displacement of the cam slide 38 which incorporates cam 32 located at the center of its width. The cam 32 interfaces with the cam surfaces on the cantilever spreader beams 30 that are integral with the spreader slide 42. By continuing the displacement of the cam 32 the cantilever spreader beams 30 are forced laterally apart. Cantilever spreader end parts 36, integral with the distal end of the cantilever spreader beams 30, in doing so apply a force and induce a result and deflection of the staple 10. By displacing the staple sides laterally, the staple legs, which are reacting against the reaction form 34, rotate (as shown in FIG. 4) about a reaction point to arrive at the horizontal position shown in FIGS. 3 and 10. The staple 10 at this stage is fully inserted into the tissue 58 and has a closed rectangular form 54 or the open legged form illustrated in FIG. 10.

The staple 10 may next be preloaded to produce the desired compression on the captured tissue 58. This feature is critical in that it allows the staple 10 to accommodate variations in tissue thickness while still achieving the desired/optimum tissue preload. In this regard, it is conceived that a load/force sensor or a gap/proximity sensor may be used to control the amount of compression. The preload of the staple 10 is preformed by displacing the preload slide 44 such that the preload die 46 impacts the bridge 12 of the staple 10 the bridge 12 is plastically deformed, as a result, and compresses the tissue 58. The amount of staple preload may be varied by altering the amount of the displacement of the preload slide 44. The injection mechanism is shown in the preloaded state in FIG. 5. As previously mentioned, preloading can also be accomplished by inducing tissue lateral stress during stapling. Once the "thinned" tissue is released, after stapling, the preloading state results.

The stapler 26 must also reliably release the staple but the design must assure that premature release is not possible. In one embodiment, this task is accomplished by fully constraining the staple 10 until the time of desired release at which time the injector slide 40 is displaced to apply a load to the top of each end of the staple bridge 12. This load induces an out of plane deflection of the cantilever spreader beams 30, that allows the staple 10 to ride up and over the end parts 36. Additional clearance may be provided for staple release by allowing the staple to deflect the cover 48 upward out of plane. In another embodiment, top slide 61 is operated as previously described. In any event, the staple 10 is now free of the stapler 26 and the stapler 26 may be retracted from the tissue 58 surface.

While the staple and stapler of the present invention have been disclosed in connection with surgical stapling of tissue, it is obvious that they can be used in other mediums as well. The present invention provides an improved stapler which can be easily manipulated and is useful in any environment where the material to be joined will be damaged by the normal tearing and pinching action of the prior art staples. The ability of the staple of the present invention to maintain a near constant width upon penetration and during staple closure/forming is an advantage in any environment where tearing and staple to staple spacing must be minimized.

While the present invention has been disclosed in connection with the preferred embodiment thereof, it should be understood that there may be other embodiments which fall within the spirit and scope of the invention as defined by the following claims.

What is claimed is:

1. A staple, comprising:
   (a) a bridge part having two ends;
   (b) a proximal arcuate section extending outwardly from each end of said bridge part, said proximal arcuate sections being spaced apart by a first distance;
   (c) a distal arcuate section extending inwardly from each of said proximal arcuate sections, said distal arcuate sections facing one another and being spaced apart by a second distance which is less than said first distance; and
   (d) a leg extending from each of said distal arcuate sections away from said bridge part and perpendicular thereto, said legs being parallel with one another and spaced apart by a distance equal to said first distance; such that when an outwardly directed force is applied to each of said distal arcuate sections, said distal arcuate sections become straight, parallel with one another, spaced by a distance equal to said first distance, and perpendicular to said bridge part, and said legs turn inwardly and become parallel with said bridge part.

2. The staple of claim 1, wherein the bridge part comprises a generally U-shaped central portion having opposite ends and at least one arcuate part.

3. The staple of claim 1 wherein the first distance is between 1.65 mm to 2.0 mm.

4. The staple of claim 1 wherein the staple is generally 150 microns in diameter.

5. An open staple for suturing living tissue comprising:
   (a) a rectilinear bridge part having two ends;
   (b) an S-shaped side part extending downwardly from each end of said rectilinear bridge part, with the upper curved portion of each side part connected to a respective end of said bridge part and facing inwardly while curving outwardly, and the lower-curved portion of each side part facing outwardly and curving inwardly, wherein the upper curved portions are spaced apart from each other by a first distance which is greater than a distance by which the lower curved portions are spaced apart from each other;
   (c) a leg extending from each of said lower curved portions away form said bridge part and perpendicular thereto, said legs being parallel with one another and spaced apart by a distance equal to said first distance; such that when an outwardly directed force is applied to each of said lower curved portions, said lower portions become straight, parallel to one another, spaced by a distance equal to said first distance, and perpendicular to said rectilinear bridge part, and said legs turn inwardly and become parallel with said rectilinear bridge part.

6. The staple of claim 5 wherein the first distance is between 1.65 mm to 2.0 mm.

7. The staple of claim 5 wherein the staple is generally 150 microns in diameter.

8. A staple, comprising:

(a) a bridge part having two ends;

(b) a side part extending downwardly from each end of said bridge part, each side part including a first portion connected to a respective end of said bridge part and extending perpendicular thereto, and a second portion extending from said first portion and curving outwardly therefrom, wherein the first portions are spaced from each other by a first distance which is less than a distance by which the second portions are spaced part from each other; and (c) a leg extending from each of said second portions away from said bridge part and perpendicular thereto, said legs being parallel with one another and spaced apart by a distance equal to said first distance; such that when an inwardly directed force is applied to each said second portion, said second portions became straight, parallel with one another, spaced by a distance equal to said first distance, and perpendicular to said bridge part, and said legs turn inwardly and became parallel with said bridge part.

* * * * *

UNITED STATES PATENT AND TRADEMARK OFFICE
CERTIFICATE OF CORRECTION

PATENT NO. : 5,695,524
DATED : December 9, 1997
INVENTOR(S) : Mark Kelley, et al It is certified that error appears in the above-identified patent and that said Letters Patent is hereby corrected as shown below:

In Column 1, Line 18 of the Patent, change the words "into an are" to --into an arc--.

In Column 2, Line 9 of the Patent, change the words "abovedescribed" to --above-described--.

In Column 4, Line 5 of the Patent, change the word "2.0 mm" to --2.0mm--.

Signed and Sealed this

Nineteenth Day of May, 1998

Attest:

BRUCE LEHMAN

Attesting Officer

Commissioner of Patents and Trademarks